(12) United States Patent
Kikuchi et al.

(10) Patent No.: US 11,451,698 B2
(45) Date of Patent: Sep. 20, 2022

(54) MEDICAL SYSTEM AND CONTROL UNIT

(71) Applicant: Sony Corporation, Tokyo (JP)

(72) Inventors: Daisuke Kikuchi, Kanagawa (JP); Yuki Sugie, Kanagawa (JP); Yukihiro Nakamura, Kanagawa (JP); Kentaro Fukazawa, Tokyo (JP); Kenji Ikeda, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/617,528

(22) PCT Filed: Mar. 28, 2018

(86) PCT No.: PCT/JP2018/012730
§ 371 (c)(1),
(2) Date: Nov. 27, 2019

(87) PCT Pub. No.: WO2018/225346
PCT Pub. Date: Dec. 13, 2018

(65) Prior Publication Data
US 2020/0128169 A1   Apr. 23, 2020

(30) Foreign Application Priority Data

Jun. 5, 2017  (JP) .............................. JP2017-110569

(51) Int. Cl.
*H04N 5/232*  (2006.01)
*A61B 90/20*  (2016.01)
(Continued)

(52) U.S. Cl.
CPC ......... *H04N 5/23203* (2013.01); *A61B 1/045* (2013.01); *A61B 90/20* (2016.02);
(Continued)

(58) Field of Classification Search
CPC .............. A61B 90/20; A61B 2090/371; A61B 2562/06; A61B 8/5238; A61B 8/5246;
(Continued)

(56) References Cited

U.S. PATENT DOCUMENTS 5,614,943 A     3/1997 Nakamura et al.
2007/0036530 A1*  2/2007 Nakagomi ......... H04N 5/23254
                                                    396/54

(Continued)

FOREIGN PATENT DOCUMENTS

CN   106455948 A    2/2017
JP   61-268239 A    11/1986
(Continued)

OTHER PUBLICATIONS

International Search Report and Written Opinion dated May 22, 2018 for PCT/JP2018/012730 filed on Mar. 28, 2018, 12 pages including English Translation of the International Search Report.
Extended European Search Report dated May 12, 2020, in corresponding European Patent Application No. 18813871.3.

*Primary Examiner* — John W Miller
*Assistant Examiner* — Humam M Satti
(74) *Attorney, Agent, or Firm* — Xsensus LLP

(57) ABSTRACT

In a case where a plurality of imaging apparatuses is used for a surgery, the appearance is regulated between images captured by the respective imaging apparatuses.
According to the present disclosure, a medical system is provided, the medical system including a plurality of surgical imaging apparatuses and a control unit to which each of the surgical imaging apparatuses is connected, the control unit including a signal processing unit that links images captured by the respective surgical imaging apparatuses. With this configuration, in a case where a plurality of imaging apparatuses is arranged for a surgery, it becomes (Continued)

possible to regulate the appearance between images captured by the respective imaging apparatuses.

19 Claims, 14 Drawing Sheets

(51) Int. Cl.
*A61B 1/045* (2006.01)
*H04N 5/247* (2006.01)
*G02B 21/00* (2006.01)
*G02B 21/36* (2006.01)
*H04N 5/225* (2006.01)

(52) U.S. Cl.
CPC ......... *H04N 5/247* (2013.01); *G02B 21/0012* (2013.01); *G02B 21/367* (2013.01); *H04N 2005/2255* (2013.01)

(58) Field of Classification Search
CPC ........ A61B 8/5261; A61B 2017/00225; A61B 2090/364; A61B 90/36; A61B 90/361; A61B 1/045; A61B 1/000095; A61B 1/00006; A61B 1/0005; G02B 21/0012; G02B 21/367; G02B 23/26; H04N 5/23203; H04N 5/23258; H04N 2209/00; H04N 5/247; H04N 2005/2255
USPC .................................. 348/77, 65, 64, 72, 73
See application file for complete search history.

(56) References Cited

U.S. PATENT DOCUMENTS

| | | | |
|---|---|---|---|
| 2008/0198219 A1* | 8/2008 | Yoshida | H04N 13/133 348/43 |
| 2012/0200683 A1 | 8/2012 | Oshima et al. | |
| 2013/0041226 A1* | 2/2013 | McDowall | A61B 1/055 600/166 |
| 2013/0165753 A1 | 6/2013 | Takahashi | |
| 2013/0286172 A1 | 10/2013 | Sasaki | |
| 2014/0005484 A1* | 1/2014 | Charles | A61B 1/00039 600/201 |
| 2014/0320684 A1 | 10/2014 | Chatenever et al. | |
| 2014/0350338 A1 | 11/2014 | Tanaka et al. | |
| 2017/0143442 A1* | 5/2017 | Tesar | H04N 13/344 |
| 2017/0245761 A1* | 8/2017 | Piron | A61B 6/501 |

FOREIGN PATENT DOCUMENTS

| | | |
|---|---|---|
| JP | 7-261094 A | 10/1995 |
| JP | 2004-24835 A | 1/2004 |
| JP | 2011-055939 A | 3/2011 |
| JP | 2012/005108 A | 1/2012 |
| JP | 2012-55498 A | 3/2012 |
| JP | 2016-174809 A | 10/2016 |
| WO | 2016/098736 A1 | 6/2016 |
| WO | 2016/154589 A1 | 9/2016 |
| WO | 2016/190022 A1 | 12/2016 |
| WO | 2016/194446 A1 | 12/2016 |

* cited by examiner

MEDICAL SYSTEM AND CONTROL UNIT

CROSS-REFERENCE TO RELATED APPLICATIONS

The present application is based on PCT filing PCT/JP2018/012730, filed Mar. 28, 2018, which claims priority to JP 2017-110569, filed Jun. 5, 2017, the entire contents of each are incorporated herein by reference.

TECHNICAL FIELD

The present disclosure relates to a medical system and a control unit.

BACKGROUND ART

Conventionally, for example, Patent Document 1 below discloses that, in an endoscope apparatus that can use a probe-type endoscope, two images are accurately matched and a composite image is generated regardless of the position of a probe tip portion and the degree of curvature of a scope tip portion.

CITATION LIST

Patent Document

Patent Document 1: Japanese Patent Application Laid-Open No. 2011-55939

SUMMARY OF THE INVENTION

Problems to be Solved by the Invention

In a medical imaging apparatus, there are cases where a plurality of cameras is used at the same time. For example, in a brain surgery or the like, there is a case where an exoscope is used when a near part of the surgical field is observed, and an endoscope is used when a deep part of the surgical field is observed. In such cases, when images captured by a plurality of cameras are displayed as they are, two images have different appearances, which makes an observer feel uncomfortable. Furthermore, for example, even if the same subject is imaged and displayed, disadvantages such as difficulty in recognizing that subjects having different appearances are the same subject and difficulty in recognizing the relationship between the two images are caused.

The technology disclosed in Patent Document 1 above specifies the enlargement/reduction magnification and the phase shift amount on the basis of the protruding length of the probe tip portion and the curvature angle of the scope tip portion, and makes the size of an observation object such as a lesion coincident with the size of an observation object in a normal observation image. The technology disclosed in Patent Document 1 is to make the image sizes coincident with each other in a case where the positional relationship of one image with respect to another image is defined in advance, but does not at all assume any measure for regulating the appearance between two images according to the images captured by different apparatuses.

Therefore, in a case where a plurality of imaging apparatuses is used for a surgery, it has been expected to regulate the appearance between images captured by the respective imaging apparatuses.

Solutions to Problems

According to the present disclosure, a medical system is provided, the medical system including a plurality of surgical imaging apparatuses and a control unit to which each of the surgical imaging apparatuses is connected, the control unit including a signal processing unit that links images captured by the respective surgical imaging apparatuses.

Furthermore, according to the present disclosure, a control unit to which each of a plurality of surgical imaging apparatuses is connected is provided, the control unit including a signal processing unit that links images captured by the respective surgical imaging apparatuses.

In addition, according to the present disclosure, a medical system is provided, the medical system including a plurality of surgical imaging apparatuses, a control unit to which each of the surgical imaging apparatuses is connected, and an integrated apparatus to which each of a plurality of the control units is connected, the integrated apparatus including a signal processing unit that links images captured by the respective surgical imaging apparatuses.

Effects of the Invention

As described above, according to the present disclosure, in a case where a plurality of imaging apparatuses is used for a surgery, it is possible to regulate the appearance between images captured by the respective imaging apparatuses.

Note that the above-mentioned effect is not necessarily limited, and any effects indicated in the present description or other effects that can be learned from the present description may be exhibited together with the above-mentioned effect or instead of the above-mentioned effect.

MODE FOR CARRYING OUT THE INVENTION

Figure 1:
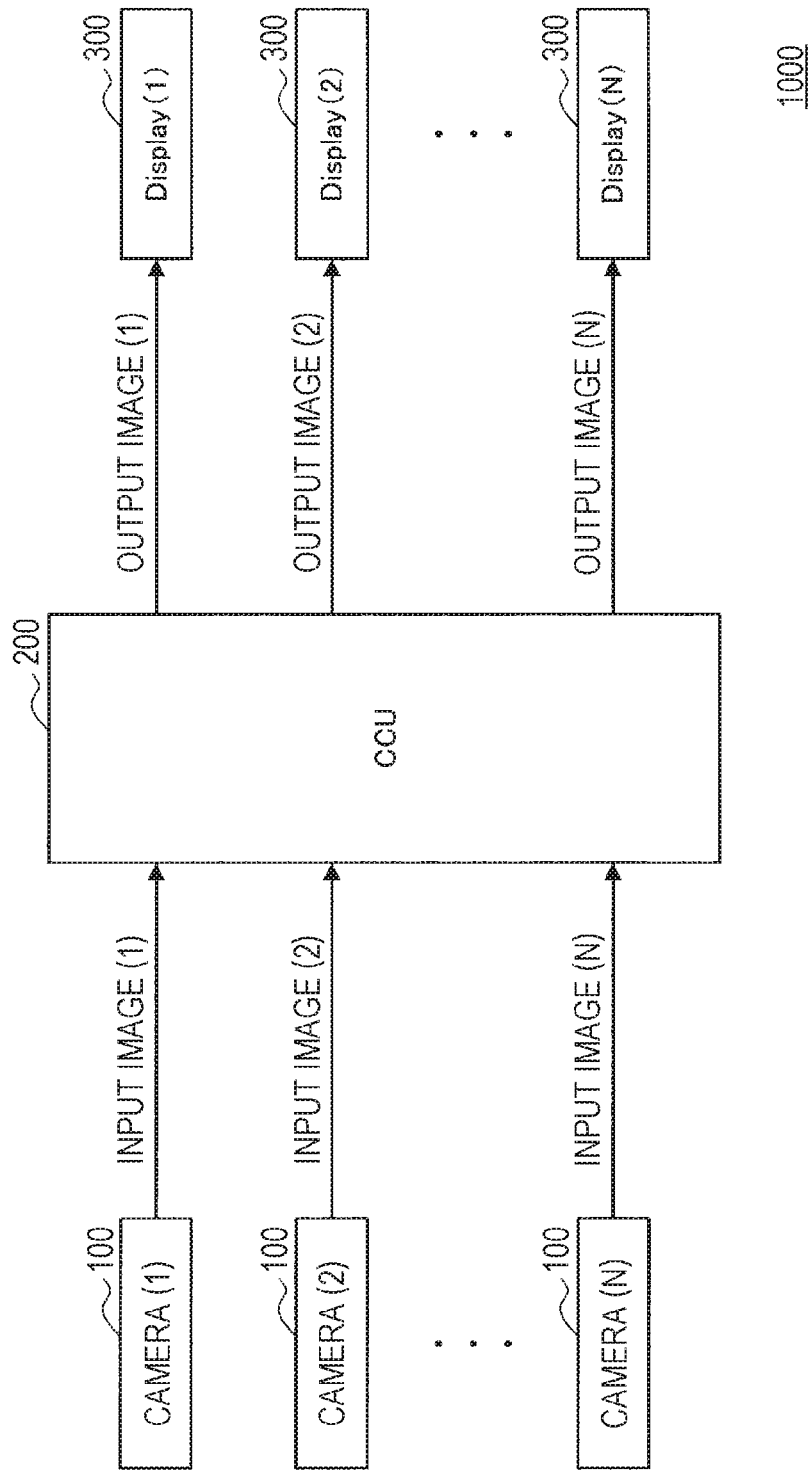
FIG. 1 is a schematic diagram illustrating an outline of the configuration of a surgical system according to each embodiment of the present disclosure.

Hereinafter, favorable embodiments of the present disclosure will be described in detail with reference to the accompanying drawings. Note that, in the present description and the drawings, constituent elements having substantially the same functional configuration will be denoted by the same reference numeral and redundant description will be omitted.

Note that the description will be given in the following order.

1. Configuration Example of System
2. Configuration of Signal Processing Unit
3. Adjustment of Color between Exoscopic Image and Endoscopic Image
4. Adjustment of Shake between Exoscopic Image and Endoscopic Image
5. Adjustment of Brightness and Contrast between Exoscopic Image and Endoscopic Image
6. Adjustment of Sense of Resolution and Depth of Field between Exoscopic Image and Endoscopic Image
7. Adjustment of Noise between Exoscopic Image and Endoscopic Image
8. Adjustment of Orientation and Angle of View between Exoscopic Image and Endoscopic Image
9. Adjustment of Sense of Depth between Exoscopic Image and Endoscopic Image
10. Configuration Example including Plurality of CCUs, to Each of which Plurality of Camera Units is Connected

1. Configuration Example of System

First, an outline of the configuration of a surgical system 1000 according to each embodiment of the present disclosure will be described with reference to FIG. 1. As illustrated in FIG. 1, this surgical system 1000 is configured from a plurality of camera units 100, a CCU (control unit) 200 to which a plurality of cameras can be connected and which is capable of a plurality of outputs, and a plurality of monitors 300. The surgical system 1000 generates a plurality of output images by signal processing from information in a plurality of input signals from the plurality of camera units 100, and outputs the generated output images to the monitors 300.

Figure 2:
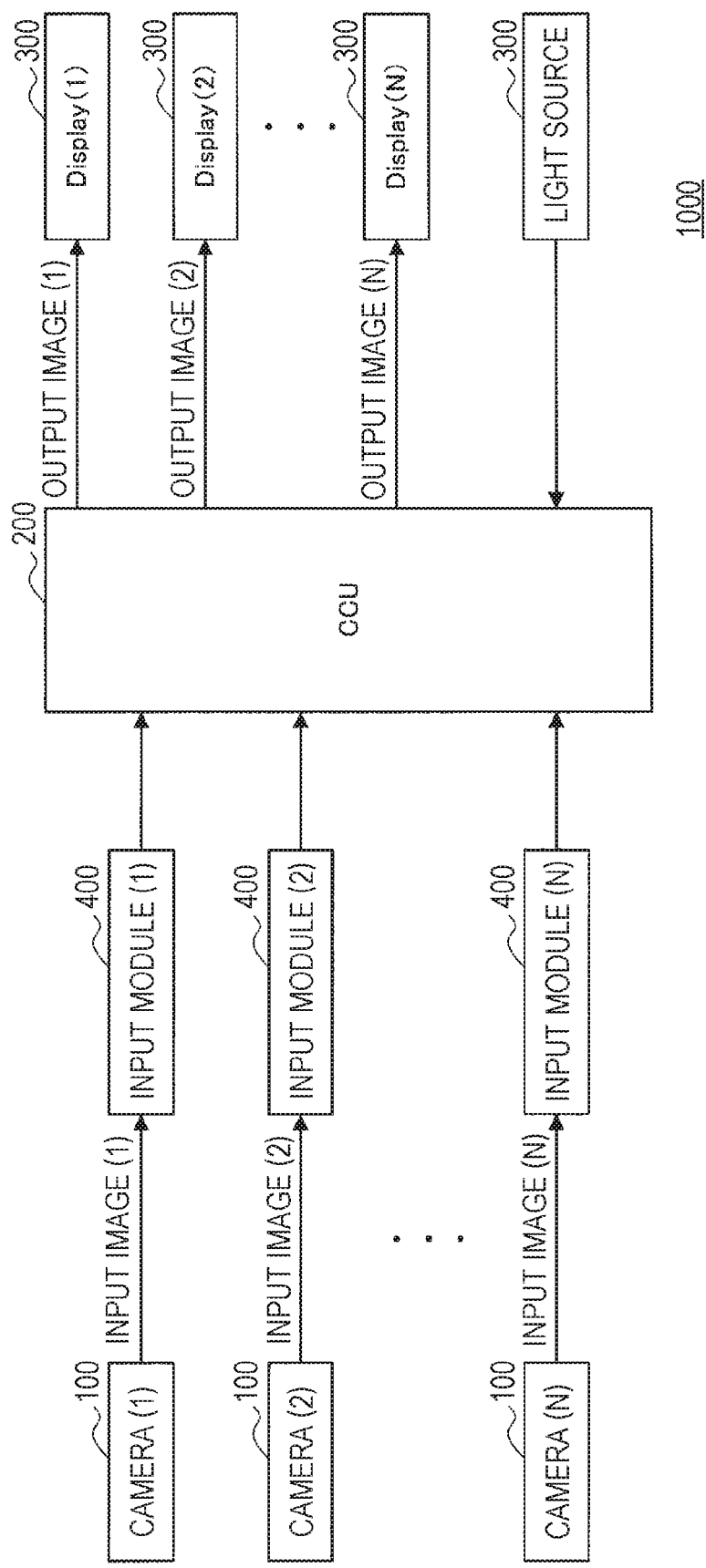
FIG. 2 is a schematic diagram illustrating a configuration further including an input module that relays between a camera unit and a camera control unit (CCU), in addition to the configuration in FIG. 1.

FIG. 2 is a schematic diagram illustrating a configuration example of a system further including an input module (camera head unit) 400 that relays between the camera unit 100 and the CCU 200 in addition to the configuration in FIG. 1, in which the surgical system 1000 inputs an image to the CCU 200 after performing a pre-process in the input module 400. The input module 400 is used, for example, to ensure compatibility between the camera unit 100 and the CCU 200.

In the present embodiment, the plurality of camera units 100 is a plurality of cameras used for surgery and, for example, represents an endoscope (a rigid endoscope or a flexible endoscope), an extracorporeal scope (exoscope), a microscope, a surgical field camera, and the like. The surgical system 1000 may include a light source apparatus that irradiates the subject when the camera unit 100 images the subject.

The plurality of camera units 100 is sometimes used at the same time during surgery. For example, in a brain surgery or the like, there is a case where an exoscope is used when a near part of the surgical field is observed, and an endoscope is used when a deep part of the surgical field is observed. As an example, a conceivable case for a brain aneurysm in the open brain includes a case where the front side of the affected part is observed with an exoscope, and the back side of the affected part is observed by inserting an endoscope, and the like. In such a case, in the present embodiment, a process of adapting the appearance of respective images between the plurality of camera units 100 is performed. In different terms, in the present embodiment, a process of linking the images of the plurality of camera units 100 with each other is performed. Examples of the combination of the plurality of camera units 100 used at the same time include an endoscope and an exoscope, an endoscope and a surgical microscope, a rigid endoscope and a flexible endoscope, and an endoscope, a surgical field camera, and the like. Note that, while the endoscope mirror is suitable for the case of observing the details of the subject, if the endoscope is moved away from the subject in order to take an image of a wider range, the image is distorted. The exoscope includes a dedicated optical system and is capable of capture an image without causing distortion in such a case; there is thus an advantage that, for example, it is easy to perform a surgery because a sufficient distance can be ensured between the subject and the exoscope. Furthermore, the surgical field camera is a camera that takes an image of the entire surgical situation.

2. Configuration of Signal Processing Unit

Figure 3:
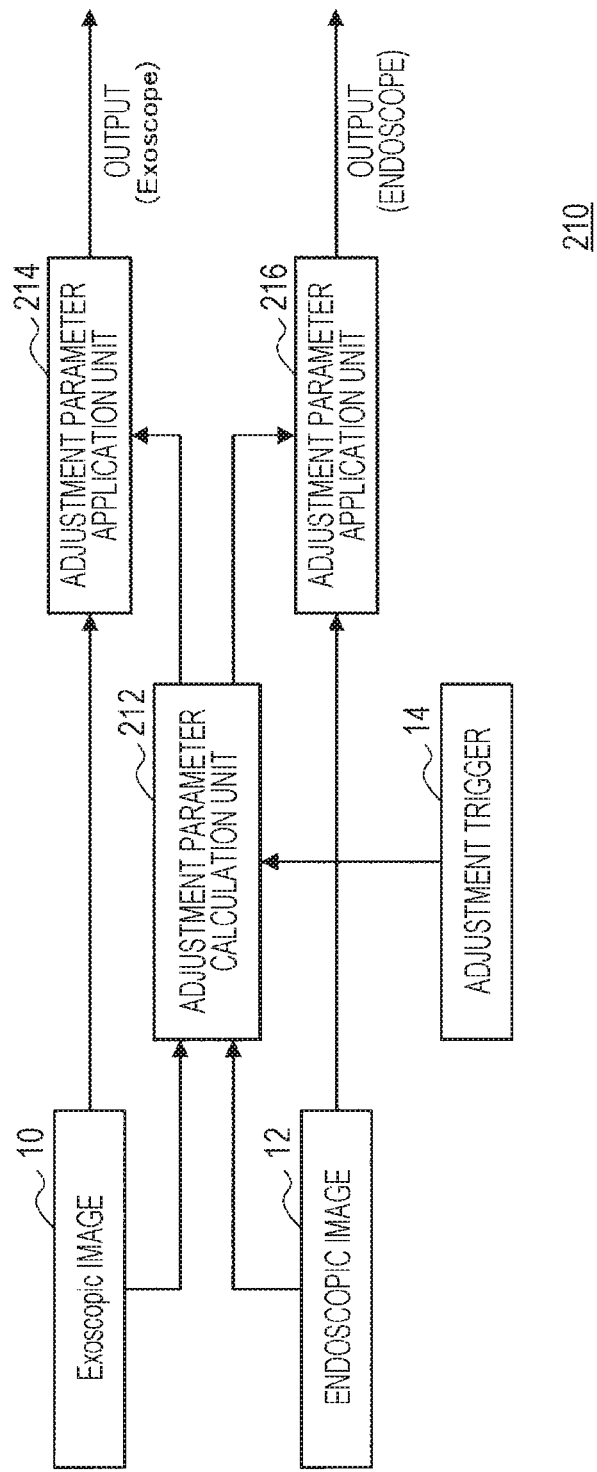
FIG. 3 is a schematic diagram illustrating the configuration and action of a signal processing unit in the CCU.

FIG. 3 is a schematic diagram illustrating the configuration and action of the signal processing unit 210 in the CCU 200 in a system in which two cameras, namely, an exoscope and an endoscope are connected to the CCU 200 as the plurality of camera units 100. The signal processing unit 210 is provided in the CCU 200 to which the plurality of camera units 100 is connected, and performs a process so as to adapt the appearance between an image generated on the basis of an imaging signal obtained from one of the camera units 100 and an image generated on the basis of an imaging signal obtained from the other of the camera units 100.

As illustrated in FIG. 3, the signal processing unit 210 includes an adjustment parameter calculation unit 212, an adjustment parameter application unit 214, and an adjustment parameter application unit 216. The adjustment parameter calculation unit 212 accepts inputs of image information 10 from the exoscope (hereinafter also referred to as an exoscopic image) and image information 12 from the endoscope (hereinafter also referred to as an endoscopic image). Furthermore, an adjustment trigger 14 is input to the adjustment parameter calculation unit 212. The adjustment trigger 14 is information defined from the outside or an input image, and is information serving as a trigger for performing adjustment using an adjustment parameter. For example, in a case where it is detected that both of the exoscopic image 10 and the endoscopic image 12 have the same subject, the adjustment trigger occurs.

When the adjustment trigger 14 occurs, a process of adapting the appearance between the exoscopic image 10 and the endoscopic image 12 is performed. The adjustment parameter is a parameter for performing the process of adapting the appearance between the exoscopic image 10 and the endoscopic image 12. On the other hand, in a case where the adjustment trigger 14 does not occur, the process of adapting the appearance between the exoscopic image 10 and the endoscopic image 12 is not performed, and the exoscopic image 10 and the endoscopic image 12 are processed independently.

When the adjustment trigger 14 occurs and is input to the adjustment parameter calculation unit 212, the adjustment parameter calculation unit 212 calculates adjustment parameters relating to the color, luminance, contrast, depth of field, noise, angle of view, image orientation, and the like from the exoscopic image 10, or the endoscopic image 12, or both of the exoscopic image 10 and the endoscopic image 12. The adjustment parameter is sent to one or both of the adjustment parameter application units 214 and 216. Upon receiving the adjustment parameter, the adjustment parameter application unit 214 applies the adjustment parameter to the exos image 10. Furthermore, upon receiving the adjustment parameter, the adjustment parameter application unit 216 applies the adjustment parameter to the endoscopic image 12. As described above, the signal processing unit 210 applies the adjustment parameter to one or both of the exoscopic image 10 and the endoscopic image 12, and generates an output image of each image. With this process, the appearance can be adapted between the exoscopic image 10 and the endoscopic image 12, and it is possible to prevent inconsistency from being caused in the appearance of the subject when the user observes the image obtained from one of the camera units 100 after observing the image obtained from the other of the camera units 100.

In addition to a case where the exoscopic image 10 and the endoscopic image 12 have the same subject as described above, the adjustment trigger 14 can be caused to occur according to the user operation, the state (position) of an operating surgeon, information regarding a connected device, and the like. In a case where the adjustment trigger 14 is caused to occur by the user operation, the adjustment trigger 14 occurs when the user operates an operation input unit of the CCU 200. In a case where the adjustment trigger 14 is caused to occur according to the state of an operating surgeon, for example, the position of the operating surgeon is determined from the image of the surgical field camera installed in the surgical room, and the adjustment trigger 14 is caused to occur in a case where it is determined, on the basis of the position of the operating surgeon, that the operating surgeon is performing observation with the endoscope in addition to observation with the exoscope. Furthermore, in a case where the adjustment trigger is caused to occur on the basis of information regarding a connected device, identification information of the device is acquired from each of the plurality of camera units 100 connected to the CCU 200, and the adjustment trigger 14 is caused to occur in a case where a plurality of camera units 100 for which the adjustment trigger 14 is predefined to occur is connected to the CCU 200.

In a case where the appearance is adapted between the exoscopic image 10 and the endoscopic image 12, the endoscopic image 12 may be adapted with the exoscopic image 10 with the exoscopic image 10 as a reference, or the exoscopic image 10 may be adapted with the endoscopic image 12 with the endoscopic image 12 as a reference. Alternatively, each of the exoscopic image 10 and the endoscopic image 12 may be adapted with a target image serving as a reference for adapting the appearance.

3. Adjustment of Color Between Exoscopic Image and Endoscopic Image

Figure 4:
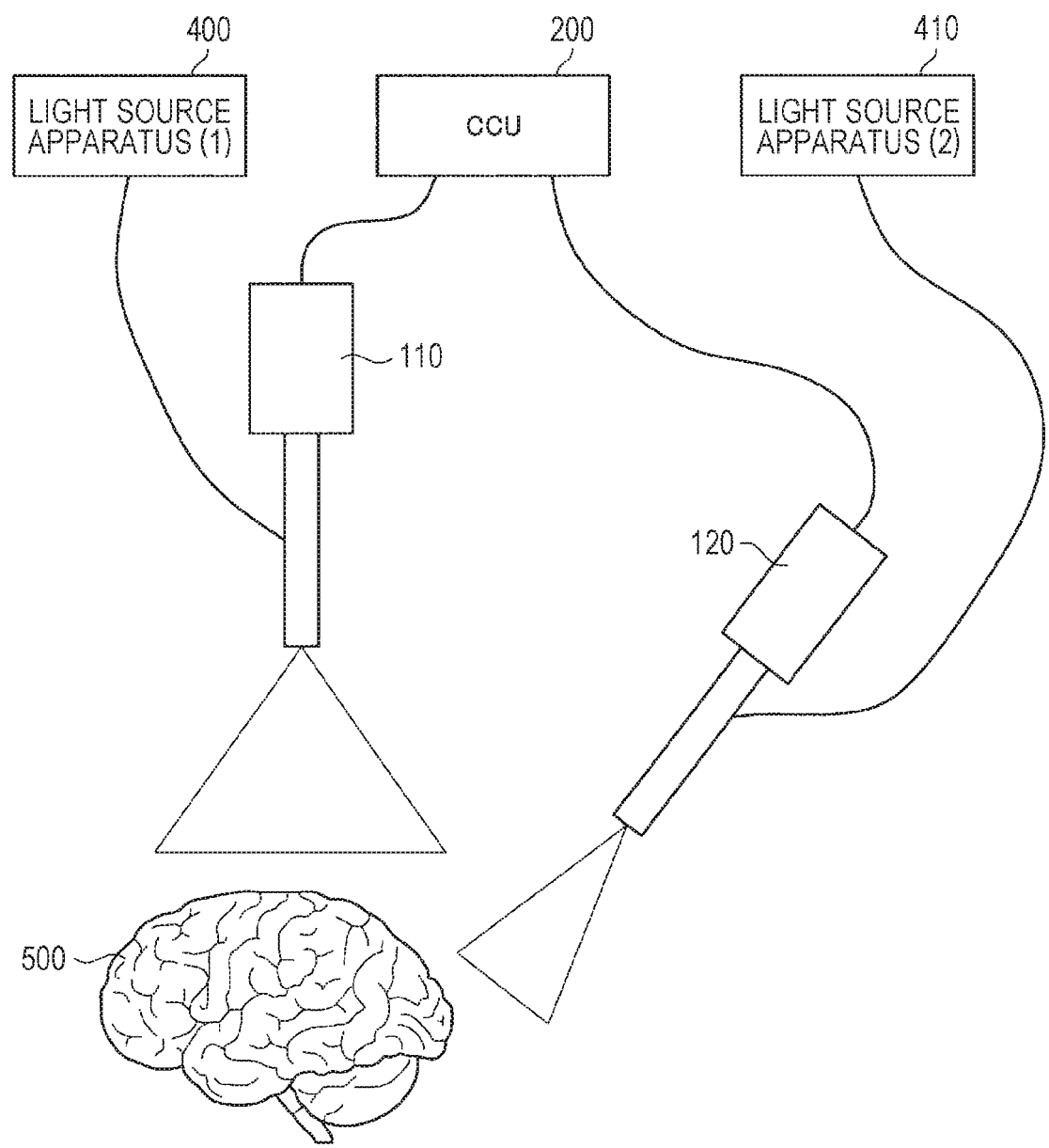
FIG. 4 is a schematic diagram illustrating a case where an exoscope and an endoscope are used together at the same time to observe a subject.

FIG. 4 is a schematic diagram illustrating a case where an exoscope 110 and an endoscope 120 are used together at the same time to observe a subject. As described above, for example, in a brain surgery or the like, since the exoscope 110 is used when a near part of the surgical field is observed, and the endoscope 120 is used when a deep part of the surgical field is observed, a case where the exoscope 110 and the endoscope 120 are used together at the same time is conceivable.

At this time, the exoscope 110 and the endoscope 120 irradiate the subject using illumination by different light sources. As illustrated in FIG. 4, the exoscope 110 irradiates the subject with illumination by a light source apparatus (1) 400, while the endoscope 120 irradiates the subject 500 with illumination by a light source apparatus (2) 410.

Furthermore, the exoscope 110 and the endoscope 120 receive light that has passed through different lenses with different sensors. For this reason, the exoscope 110 and the endoscope 120 usually have different color tones from each other even if a development process is performed with the same parameters.

Figure 5:
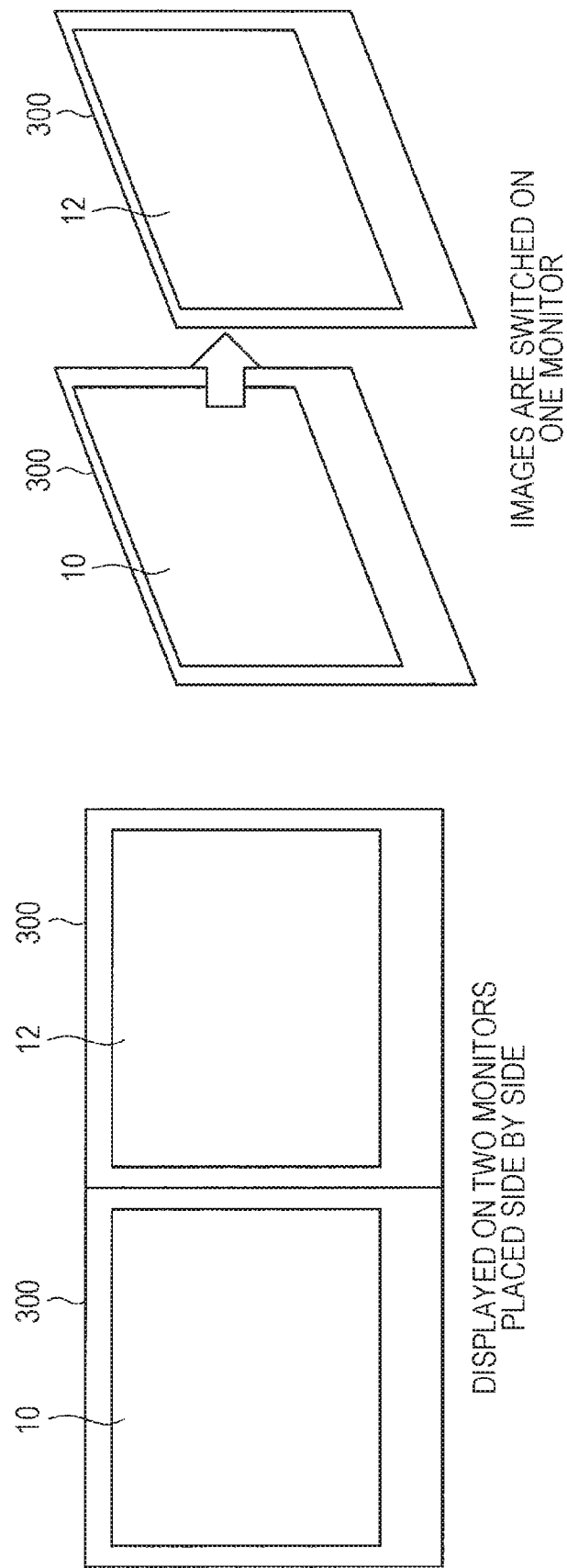
FIG. 5 is a schematic diagram illustrating methods of displaying an exoscopic image and an endoscopic image.

FIG. 5 is a schematic diagram illustrating methods of displaying the exoscopic image 10 and the endoscopic image 12. As illustrated in FIG. 5, there are following methods of displaying two images: a method in which two images are displayed on two monitors 300 placed side by side, and a method in which two images are temporally switched and displayed on one monitor 300. However, if two images with different color tones are displayed as they are, the observer will be made feel uncomfortable because the color tones of the two images are different. Furthermore, for example, even if the same subject is imaged and displayed, it becomes difficult to recognize that subjects having different color tones are the same subject, which causes difficulty in associating the two images.

Figure 6:
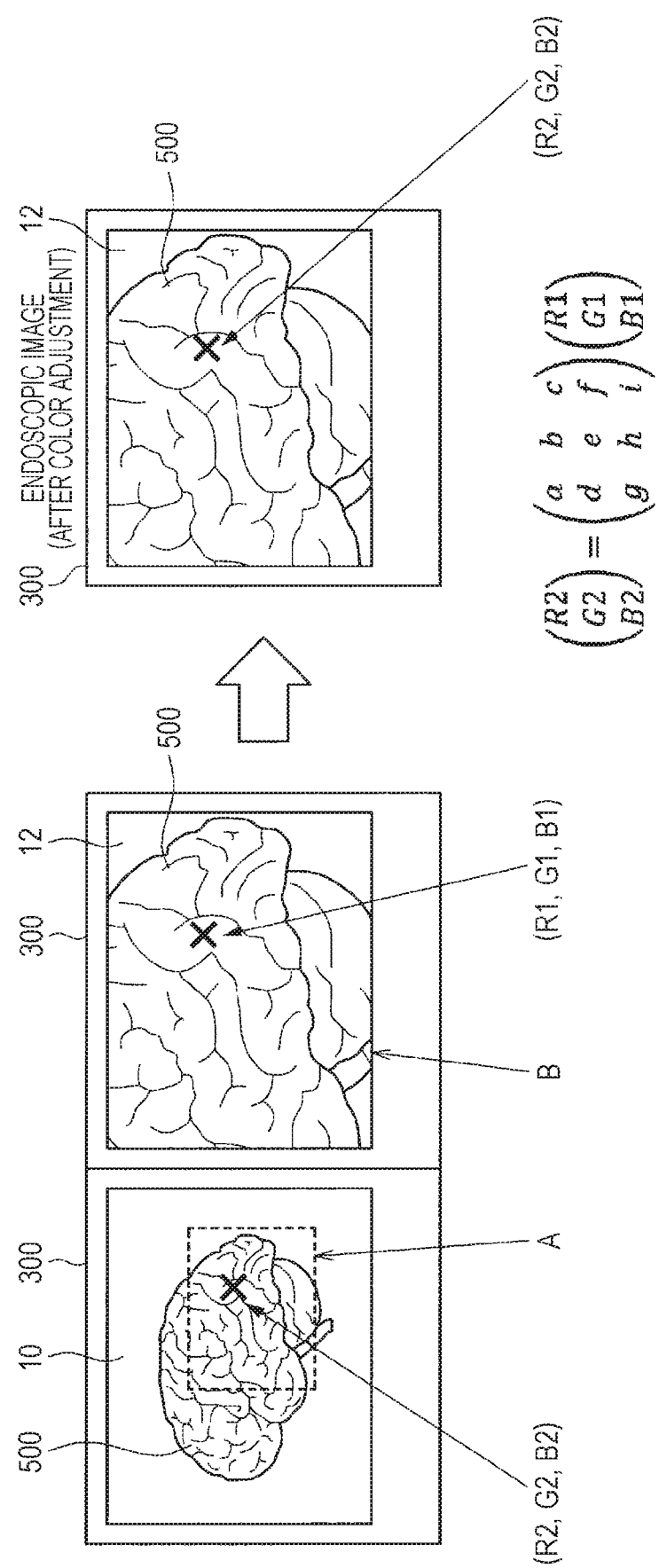
FIG. 6 is a schematic diagram illustrating a processing method for displaying the color tone of an image of the endoscope in accordance with the color tone of an image of the exoscope.

For this reason, in the present embodiment, the color tone of the endoscopic image 12 and the color tone of the exoscopic image 10 are adapted with each other when displayed. At this time, by applying the adjustment parameter to the exoscopic image, or the endoscopic image, or both of the exoscopic image and the endoscopic image, the color tone is regulated between the image of the exoscope 110 and the image of the endoscope 120. FIG. 6 is a schematic diagram illustrating a processing method for displaying the color tone of an image of the endoscope 120 in accordance with the color tone of an image of the exoscope 110.

First, it is determined whether or not the same subject and area are shown in the two images. At this time, by matching the two images, it is possible to detect whether or not the two images have the same subject, and it is possible to detect a common area. In the example illustrated in FIG. 6, it is detected by block matching that an area A of the exoscopic image 10 and an area B of the endoscopic image 12 have the same subject and are a common area.

Next, an example of a processing method in a case where the color tone of the endoscopic image 12 is adapted with the color tone of the exoscopic image 10 will be described. For the areas A and B that have been matched that both of the areas have the same position of the same subject, in a case where the respective color values at corresponding positions (indicated by x marks in FIG. 6) in the areas A and B have (R1, G1, B1) for the endoscopic image 12 and (R2, G2, B2) for the exoscopic image 10, the relationship of the colors (RGB values) between the two images can be expressed by a linear formula as illustrated in following formula (1).

[Mathematical Formula 1]

$$\begin{pmatrix} R2 \\ G2 \\ B2 \end{pmatrix} = \begin{pmatrix} a & b & c \\ d & e & f \\ g & h & i \end{pmatrix} \begin{pmatrix} R1 \\ G1 \\ B1 \end{pmatrix} \quad (1)$$

At this time, when the above equation is solved by the least squares method from the RGB values of a plurality of points, and coefficients a to i are worked out, the linear formula in formula (1) serves as a conversion formula of the RGB values from the endoscopic image 12 to the exoscopic image 10. Here, the coefficients (a to i) for conversion correspond to adjustment parameters. Therefore, the color tone of the endoscopic image 12 can be adapted with the color tone of the exoscopic image 10.

4. Adjustment of Shake Between Exoscopic Image and Endoscopic Image

Figure 7:
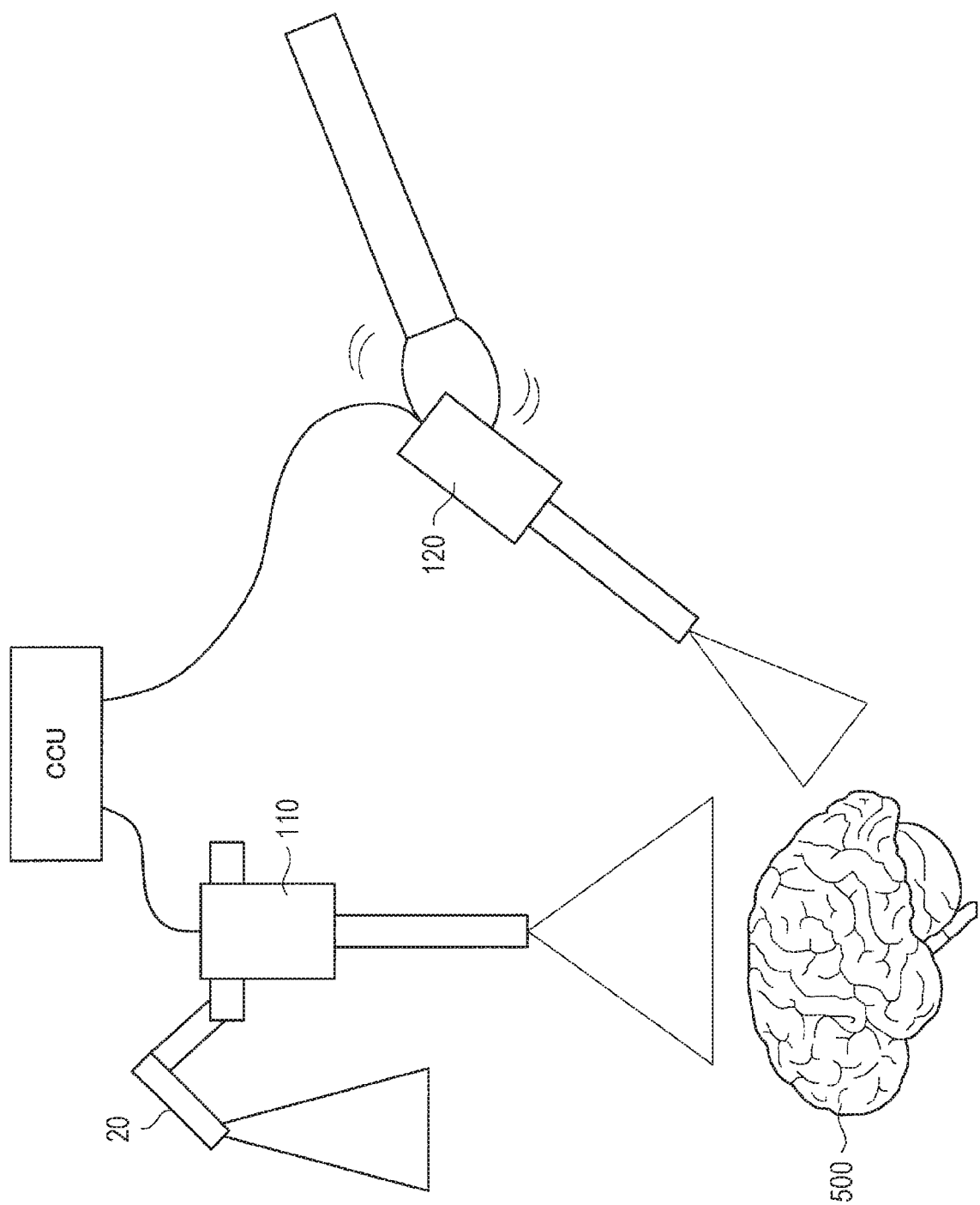
FIG. 7 is a schematic diagram for explaining an example of adapting shake between the exoscopic image and the endoscopic image.

Next, a process of adapting shake between the exoscopic image 10 and the endoscopic image 12 (camera shake removal process) in a case where the exoscope 110 and the endoscope 120 are used together at the same time to perform observation will be described on the basis of FIGS. 7 and 8. As illustrated in FIG. 7, the exoscope 110 is usually fixed by a fixing tool 20, but the endoscope 120 is held by hand by a scopist or an operating surgeon. Accordingly, shake is caused in the endoscopic image 12 in some cases.

Figure 8:
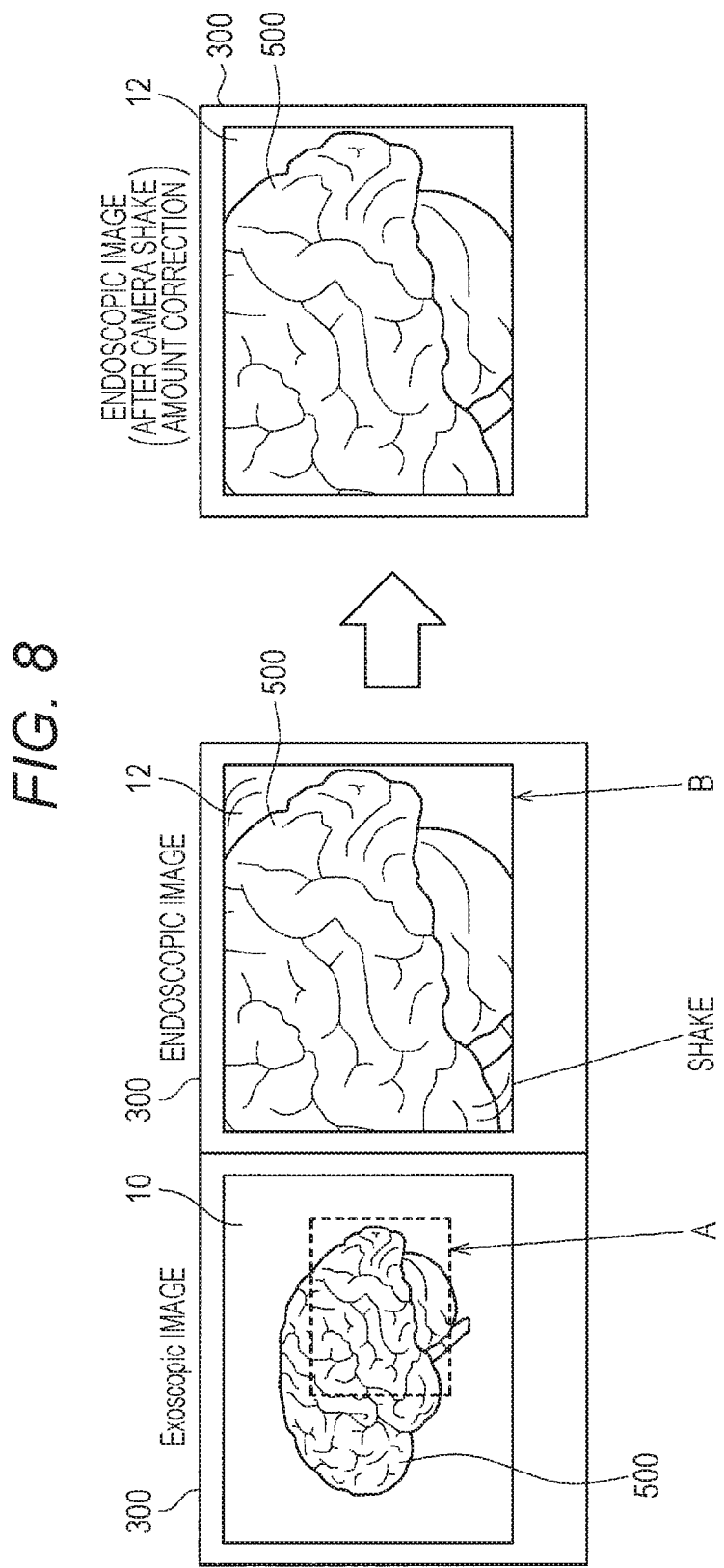
FIG. 8 is a schematic diagram for explaining an example of adapting shake between the exoscopic image and the endoscopic image.

FIG. 8 is a schematic diagram illustrating a processing method for adapting shake between the exoscopic image 10 and the endoscopic image 12. Similarly to FIG. 6, in FIG. 8, it is detected by block matching that an area A of the exoscopic image 10 and an area B of the endoscopic image 12 have the same subject and are a common area. The exoscopic image 10 of the exoscope 110 fixed by the fixing tool 20 has no shake as illustrated in the area A in FIG. 8. On the other hand, since the endoscope 120 is supported by a person, shake is caused in the endoscopic image 12 as illustrated in the area B in FIG. 8. Accordingly, the endoscopic image 12 in which shake is caused is adapted with the exoscopic image 10 in which no shake is caused.

When it is determined by block matching that the areas A and B have the same subject and area, the endoscopic image 12 is tracked in accordance with the exoscopic image 10, and shake in the endoscopic image 12 is corrected by removing a shake component of the endoscopic image 12. With this process, since shake in the endoscopic image 12 is removed in accordance with the stationary exoscopic image 10, it is possible to suppress a sense of discomfort caused when the user moves the line of sight between the exoscopic image 10 and the endoscopic image 12.

Furthermore, in a case where different areas are shown in the exoscopic image 10 and the endoscopic image 12 as a result of the block matching, shake in the endoscopic image 12 is corrected without using the exoscopic image 10. In this case, shake correction for the endoscopic image 12 is performed by recognizing shake in the endoscopic image 12 from the translational, enlargement, and rotational components of the endoscopic image 12 and performing multiplication by the inverse matrix of the shake.

Figure 9:
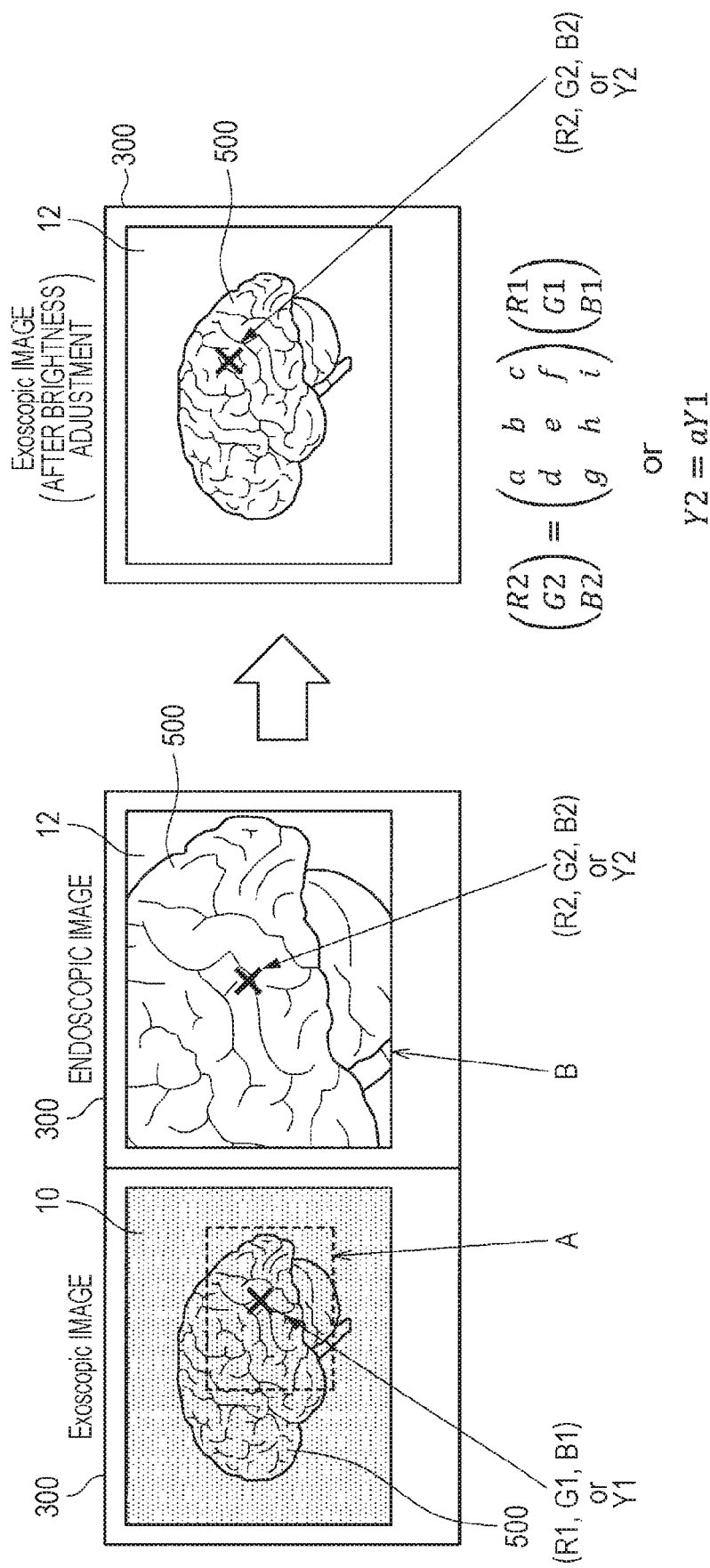
FIG. 9 is a schematic diagram illustrating an example of adapting the brightness (luminance) and contrast between the exoscopic image and the endoscopic image.

5. Adjustment of Brightness and Contrast Between Exoscopic Image and Endoscopic Image FIG. 9 is a schematic diagram illustrating an example of adapting the brightness (luminance) and contrast between the exoscopic image 10 and the endoscopic image 12. The method of calculating the brightness conversion coefficient of each color can be performed in a similar manner to the case of adapting the color tone described with reference to FIG. 6. When luminance Y obtained by conversion from the RGB values is adapted, luminance Y1 of the exoscopic image 10 is converted into luminance Y2 of the endoscopic image 12 by following formula (2). For the areas A and B that have been matched that both of the areas have the same position of the same subject, in a case where the respective luminance values at corresponding positions (indicated by x marks in FIG. 9) in the areas A and B have Y2 for the endoscopic image 12 and Y1 for the exoscopic image 10, the relationship of noise between the two images can be expressed by a linear formula as illustrated in following formula (2). Note that, in formula (2), a reference character a denotes a conversion coefficient.

$$Y2 = a \cdot Y1 \quad (2)$$

The brightness is adjusted by applying gain to a darker image depending on the relationship of R, G, and B, or Y. FIG. 9 illustrates an example in which the exoscopic image 10 is adapted with the endoscopic image 12. The conversion coefficient may be applied to the entire screen by calculating one coefficient mainly from the center area of the image, or the coefficient may be applied for each area by individually calculating the coefficient for each corresponding area in the image. By individually calculating the coefficient for each corresponding area and applying the coefficient to each area, the contrast can be made coincident between the exoscopic image 10 and the endoscopic image 12.

Figure 10:
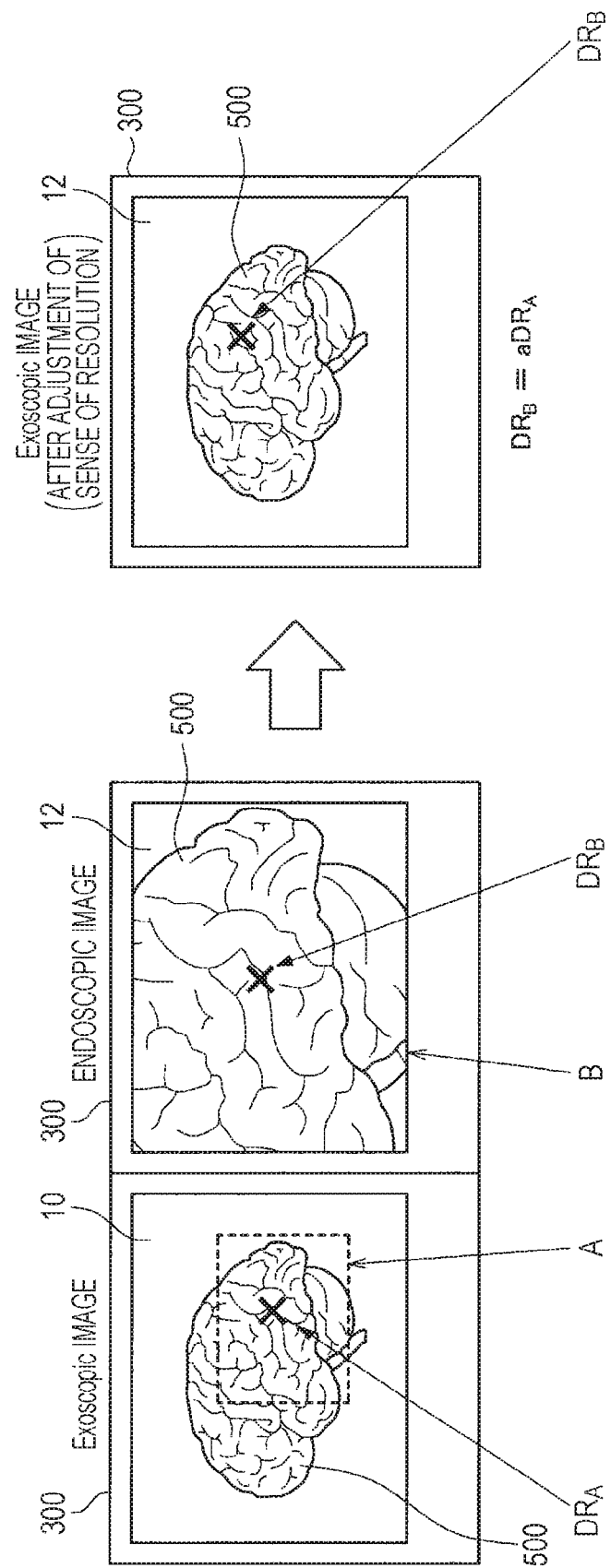
FIG. 10 is a schematic diagram illustrating an example of adapting the sense of resolution and depth of field between the exoscopic image and the endoscopic image.

6. Adjustment of Sense of Resolution and Depth of Field Between Exoscopic Image and Endoscopic Image FIG. 10 is a schematic diagram illustrating an example of adapting the sense of resolution and depth of field between the exoscopic image 10 and the endoscopic image 12. The conversion coefficient is calculated by replacing the RGB values in FIG. 6 and formula (1) with a value DR indicated by a difference between the maximum value and the minimum value of pixel values in a predetermined area around the pixel of interest. For the areas A and B that have been matched that both of the areas have the same position of the same subject, in a case where the respective values of the difference DR at corresponding positions (indicated by x marks in FIG. 10) in the areas A and B have $DR_B$ for the endoscopic image 12 and $DR_A$ for the exoscopic image 10, a difference between the maximum value and the minimum value around the pixel of interest of each image can be expressed by a linear formula as illustrated in following formula (3). Note that, in formula (3), a reference character a denotes a conversion coefficient.

$$DR_B = a \cdot DR_A \quad (3)$$

The strength of an enhancement process for an image with a smaller DR is increased depending on the DR ratio. In this case as well, the conversion coefficient may be applied to the entire screen by calculating one coefficient mainly from the center area of the image, or the coefficient may be applied for each area by individually calculating the coefficient for each corresponding area. By performing the enhancement process in accordance with one image having a deeper depth of field, the depth of field of the other image can also be increased.

7. Adjustment of Noise Between Exoscopic Image and Endoscopic Image

Figure 11:
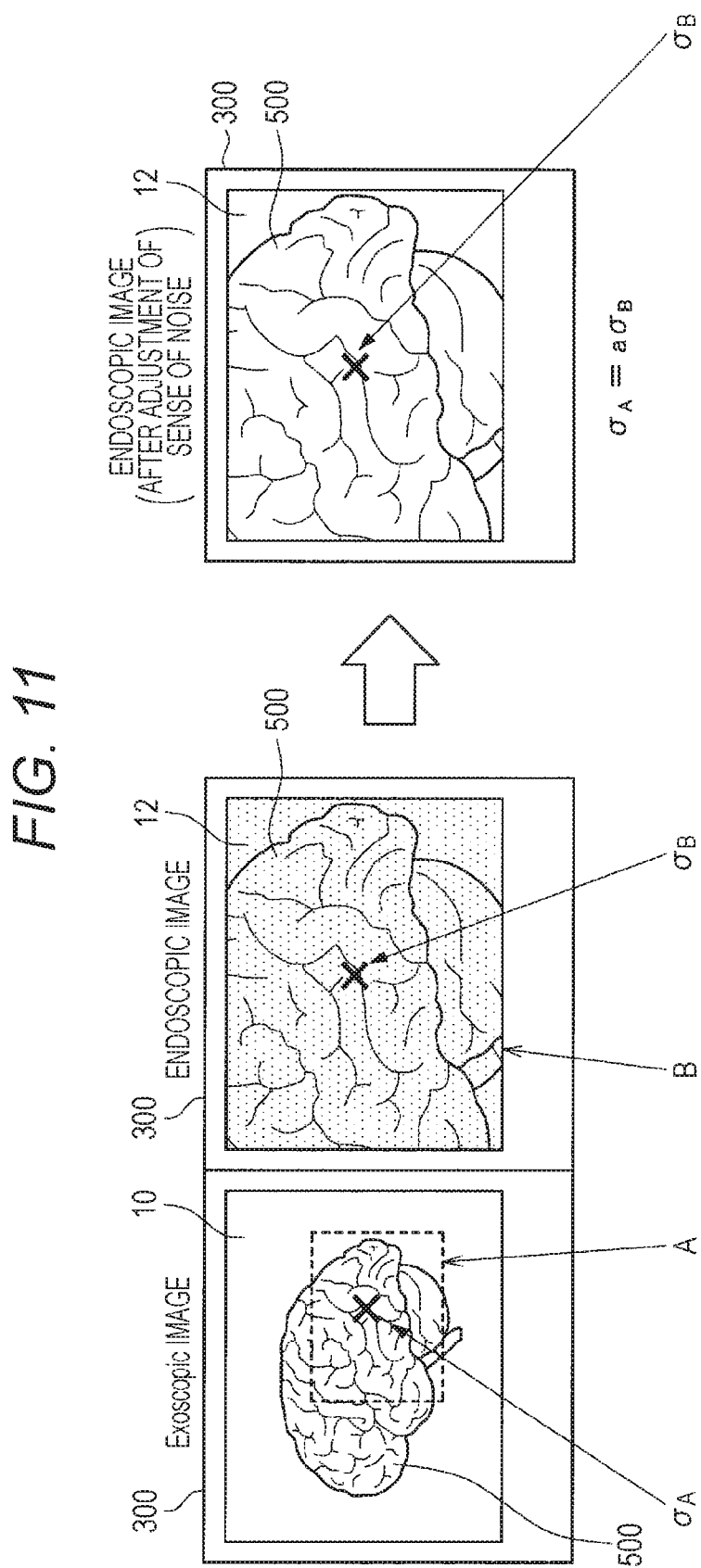
FIG. 11 is a schematic diagram illustrating an example of adapting noise between the exoscopic image and the endoscopic image.

FIG. 11 is a schematic diagram illustrating an example of adapting noise between the exoscopic image 10 and the endoscopic image 12. The method of calculating the conversion coefficient is similar to the case of adapting the color tone described with reference to FIG. 6. The conversion coefficient is calculated by assuming that the RGB values in FIG. 6 and formula (1) are replaced with a standard deviation σ of pixel values in a predetermined area around the pixel of interest.

In this case as well, for the areas A and B that have been matched that both of the areas have the same position of the same subject, in a case where the respective values of noise (standard deviation σ) at corresponding positions (indicated by x marks in FIG. 11) in the areas A and B have $\sigma_B$ for the endoscopic image 12 and $\sigma_A$ for the exoscopic image 10, the relationship of noise between the two images can be expressed by a linear formula as illustrated in following formula (4). Note that, in formula (4), a reference character a denotes a conversion coefficient.

$$\sigma_A = a \cdot \sigma_B \qquad (4)$$

The strength of noise reduction (NR) for an image with more noise is increased on the basis of the ratio of noise G. Furthermore, in addition to simply adjusting the strength of noise reduction higher or lower, when noise reduction is applied to an image with more noise, higher performance noise reduction may be performed by applying noise reduction using edge information of an image with less noise.

Figure 12:
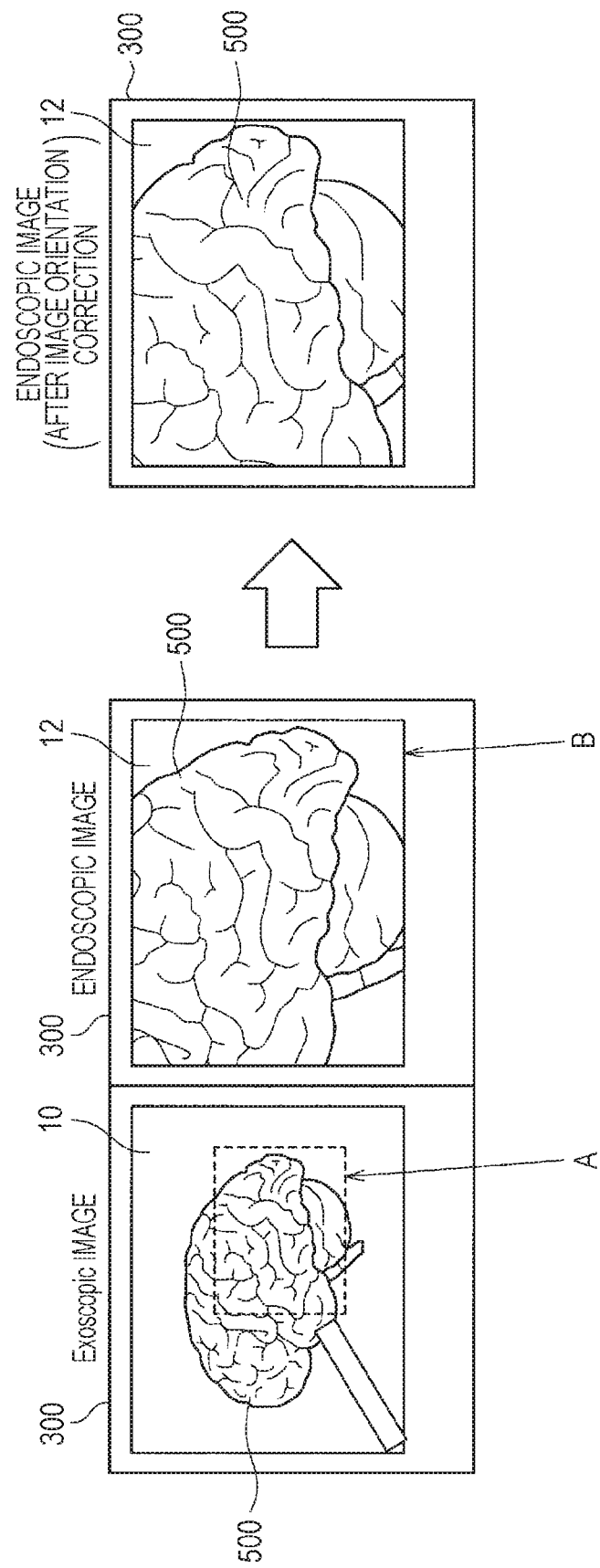
FIG. 12 is a schematic diagram illustrating an example of adapting the image orientation between the exoscopic image and the endoscopic image.

8. Adjustment of Orientation and Angle of View Between Exoscopic Image and Endoscopic Image FIG. 12 is a schematic diagram illustrating an example of adapting the image orientation and angle of view between the exoscopic image 10 and the endoscopic image 12. In this case, geometric correction is performed on the basis of the matching result between the exoscopic image 10 and the endoscopic image 12, and correction for adapting the orientation of the endoscopic image 12 with the orientation of the exoscopic image 10 is performed.

Specifically, for example, the positional relationship and the correspondence between the exoscopic image 10 and the endoscopic image 1 are acquired by block matching or the like, and geometric correction is performed depending on the result of the acquired information. In the example illustrated in FIG. 12, the image orientation of the endoscopic image 12 is fit to the image orientation of the exoscopic image 10. Note that the orientation of the endoscope shown in the exoscopic image 10 may be detected such that turning on and off of the correction is automatically switched according to the shown orientation of the endoscope. For example, if the endoscope is in an orientation in which the top and bottom are reversed between the endoscopic image 12 and the exoscopic image 10, the correction is turned on.

Figure 13:
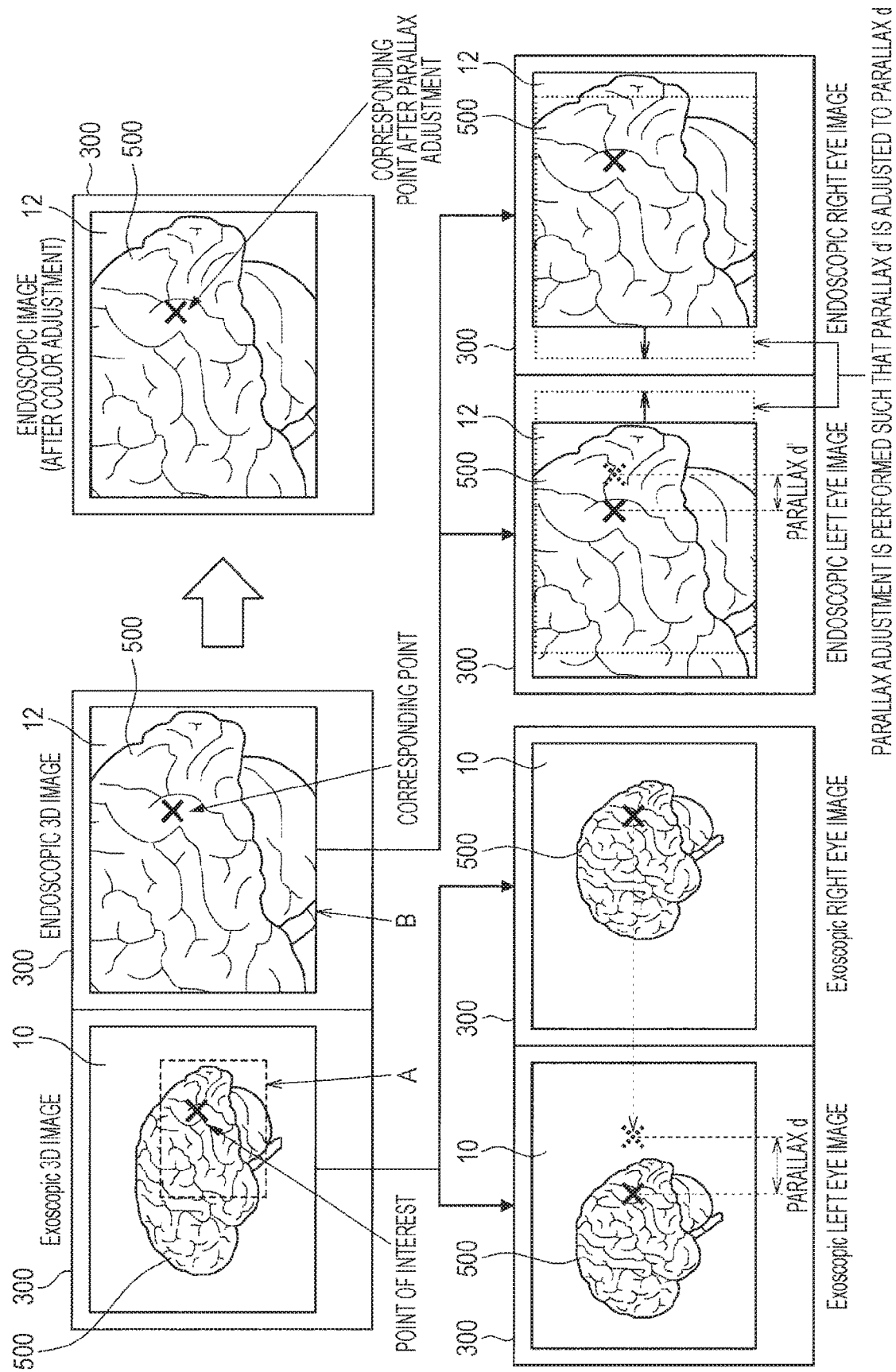
FIG. 13 is a schematic diagram illustrating an example of a case where an exoscopic image that can be taken in three dimensions (3D) and an endoscopic image that can be taken in 3D are used together.

9. Adjustment of Sense of Depth Between Exoscopic Image and Endoscopic Image FIG. 13 is a schematic diagram illustrating an example of a case where the exoscopic image 10 that can be taken in 3D and the endoscopic image 12 that can be taken in 3D are used together. For example, when the viewpoint is switched from the monitor 300 that displays the 3D image of the exoscopic image 10 to the monitor 300 that displays the 3D image of the endoscopic image 12, if the sense of depth at the point of interest on the exoscopic image 10 differs significantly from the sense of depth at the corresponding point of interest (corresponding point) on the endoscopic image 12, the user feels more uncomfortable when switching the line of sight.

For this reason, a parallax d at the point of interest is detected from left and right eye images of the exoscopic image 10 by a block matching process or the like, and similarly, a parallax d' at the corresponding point is also detected from left and right eye images of the endoscopic image 12 by a block matching process or the like. Then, a parallax adjustment process for the left and right eye images of the endoscopic image 12 is performed such that d'=d is established.

Furthermore, when the line of sight is switched from the monitor 300 that displays the 3D image of the endoscopic image 12 to the monitor 300 that displays the 3D image of the exoscopic image 10, parallax adjustment is performed on the left and right eye images of the exoscopic image 10 side such that conversely d=d' is established.

By the parallax adjustment as described above, the sense of depth is regulated to the same extent between the point of interest on the exoscopic image 10 and the corresponding point on the endoscopic image 12, and it is thus possible to mitigate the sense of discomfort when the user switches the line of sight.

In a case where the depth range differs significantly between the endoscopic image 12 and the exoscopic image 10, there is a possibility that a subject too popped or retracted is produced on the 3D image if the parallax is adapted with one of the images. Therefore, depth is estimated from the left and right eye images in each of the endoscopic image 12 and the exoscopic image 10 and, in a case where the depth range of one image is extremely larger than the depth range of the other image (a case where a difference between the depth range of one image and the depth range of the other image exceeds a predetermined value), the parallax adjustment may not be performed, or a process of lowering the degree of parallax adjustment or the like may be performed.

Note that the point of interest on the image in the present embodiment may be designated by the user using a user interface (UI) such as a pointing device, or the point of interest may be automatically detected by a line-of-sight detection device. Alternatively, a surgical instrument such as an electric knife or forceps may be detected such that, for example, the tip of an electric knife or forceps, which is often noticed by a surgeon as a user on the image, is set as a point of interest. Furthermore, a central portion of the image, which is generally likely to gather viewpoints, may be set as a point of interest.

Figure 14:
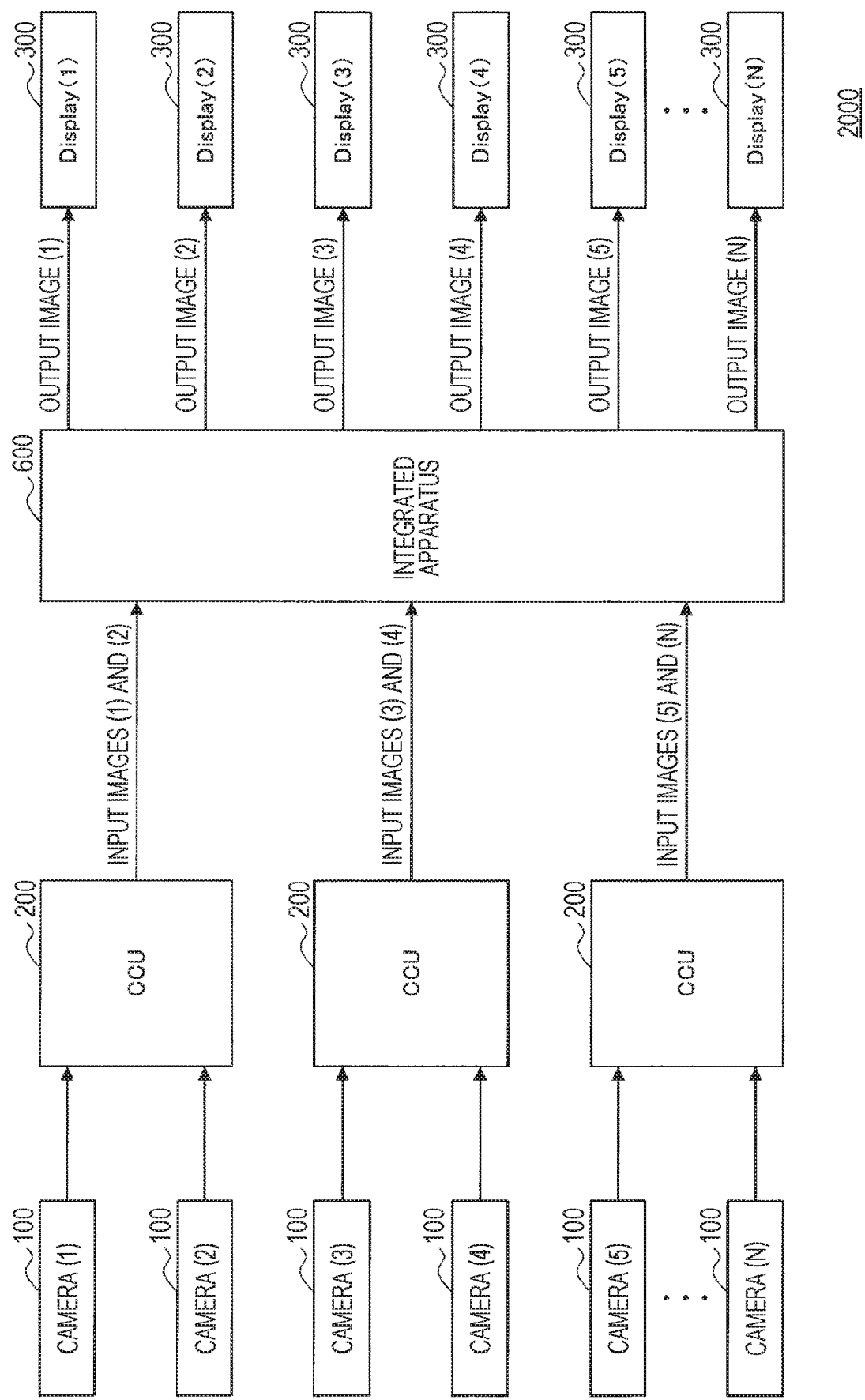
FIG. 14 is a schematic diagram illustrating a system including a plurality of CCUs, to each of which a plurality of camera units is connected, in which each CCU is connected to an integrated apparatus 600.

10. Configuration Example Including Plurality of CCUs, to Each of which Plurality of Camera Units is Connected In the above example, the surgical system 1000 in which the plurality of camera units 100 is connected to the CCU 200 has been described; however, the present disclosure can also be applied to a system including a plurality of CCUs 200, to each of which a plurality of camera units 100 is connected, in which each CCU 200 is connected to an integrated apparatus 600. FIG. 14 is a schematic diagram illustrating a system 2000 including a plurality of CCUs 200, to each of which a plurality of camera units 100 is connected, in which each CCU 200 is connected to the integrated apparatus 600.

In the system 2000 illustrated in FIG. 14, information regarding the image of the camera unit 100 is sent to the integrated apparatus 600 via the CCU 200. In the system 2000 illustrated in FIG. 14, the signal processing unit 210 illustrated in FIG. 3 is provided not in the CCU 200 but in the integrated apparatus 600. The integrated apparatus 600 performs a process of adapting the appearance between images sent from the respective camera units 100 by the function of the signal processing unit 210. Therefore, according to the system 2000 illustrated in FIG. 14, it is possible to unify the appearance of the images of the respective camera units 100 connected to the respective CCUs 200 connected to the integrated apparatus 600.

Note that, in the above description, a case where observation is performed using the exoscopic image 10 and the endoscopic image 12 together at the same time has been mainly described, however, as described with reference to FIG. 5, the present disclosure can also be applied to a case where observation is performed by switching between the exoscopic image 10 and the endoscopic image 12. In that case, the image immediately before switching is held, and various corrections for the image after switching are performed using the held image. Furthermore, the image to be corrected is not limited to the exoscopic image 10 or the endoscopic image 12, and may be changed according to the situation.

As described thus far, according to the present embodiment, in a case where two different camera units 100 are used together to image the same subject, images with the same appearance can be generated. Accordingly, in a case where two output images are placed side by side and displayed, or in a case where two output images are switched and displayed, observation without any sense of discomfort is achieved in both of the cases, and it becomes easy to learn the relationship of each of the two images with the other.

The favorable embodiments of the present disclosure have been described in detail thus far with reference to the accompanying drawings. However, the technological scope of the present disclosure is not limited to these examples. It is clear that a person with average knowledge on the technological field of the present disclosure can arrive at various variations or modifications within the range of the technological spirit disclosed in claims and as a matter of course, these variations or modifications are comprehended as part of the technological scope of the present disclosure.

Furthermore, the effects described in the present description are merely illustrative or exemplary and are not limiting. That is, the technology according to the present disclosure can exhibit other effects obvious to those skilled in the art from the description of the present description together with the above-described effects or instead of the above-described effects.

Note that configurations as described below are also within the technological scope of the present disclosure.

(1) A medical system including:

a plurality of surgical imaging apparatuses; and a control unit to which each of the surgical imaging apparatuses is connected, the control unit including a signal processing unit that links images captured by the respective surgical imaging apparatuses.

(2) The medical system according to (1) above, in which a plurality of the surgical imaging apparatuses includes at least two of an endoscope, an extracorporeal scope, a microscope, or a surgical field camera.

(3) The medical system according to (1) or (2) above, in which the signal processing unit switches whether or not to perform the linking, according to occurrence of an adjustment trigger.

(4) The medical system according to any one of (1) to (3) above, in which the signal processing unit performs a process for the linking according to occurrence of an adjustment trigger, and the adjustment trigger occurs by a user operation.

(5) The medical system according to any one of (1) to (3) above, in which the signal processing unit performs a process for the linking according to occurrence of an adjustment trigger, and the adjustment trigger occurs in a case where a plurality of the surgical imaging apparatuses images a same subject.

(6) The medical system according to any one of (1) to (3) above, in which the signal processing unit performs a process for the linking according to occurrence of an adjustment trigger, and the adjustment trigger occurs according to a state of an operating surgeon who performs a surgery.

(7) The medical system according to any one of (1) to (3) above, in which the signal processing unit performs a process for the linking according to occurrence of an adjustment trigger, and the adjustment trigger occurs according to identification information for identifying a plurality of the surgical imaging apparatuses.

(8) The medical system according to any one of (1) to (7) above, in which the signal processing unit performs a process of adapting colors between images captured by respective ones of a plurality of the surgical imaging apparatuses.

(9) The medical system according to any one of (1) to (7) above, in which the signal processing unit performs a process of adapting brightness between images captured by respective ones of a plurality of the surgical imaging apparatuses.

(10) The medical system according to any one of (1) to (7) above, in which the signal processing unit performs a process of adapting contrast between images captured by respective ones of a plurality of the surgical imaging apparatuses.

(11) The medical system according to claim 1, in which the signal processing unit performs a process of adapting resolution between images captured by respective ones of a plurality of the surgical imaging apparatuses.

(12) The medical system according to any one of (1) to (7) above, in which the signal processing unit performs a process of adapting noise between images captured by respective ones of a plurality of the surgical imaging apparatuses.

(13) The medical system according to any one of (1) to (7) above, in which the signal processing unit performs a process of adapting a depth of field between images captured by respective ones of a plurality of the surgical imaging apparatuses.

(14) The medical system according to claim 1, in which the signal processing unit performs a process of adapting a shake amount between images captured by respective ones of a plurality of the surgical imaging apparatuses.

(15) The medical system according to any one of (1) to (7) above, in which the signal processing unit performs a process of adapting a depth between stereoscopic images captured by respective ones of a plurality of the surgical imaging apparatuses.

(16) The medical system according to any one of (1) to (7) above, in which the signal processing unit performs a process of adapting an angle of view between images captured by respective ones of a plurality of the surgical imaging apparatuses.

(17) The medical system according to any one of (1) to (16) above, in which the signal processing unit links an image captured by one of a plurality of the surgical imaging apparatuses with an image captured by another one of the plurality of the surgical imaging apparatuses as a reference.

(18) The medical system according to any one of (1) to (16) above, in which the signal processing unit links images captured by a plurality of the surgical imaging apparatuses with an arbitrary desired image as a reference.

(19) A control unit to which each of a plurality of surgical imaging apparatuses is connected, the control unit including a signal processing unit that links images captured by the respective surgical imaging apparatuses.

(20) A medical system including:
a plurality of surgical imaging apparatuses;
a control unit to which each of the surgical imaging apparatuses is connected; and
an integrated apparatus to which each of a plurality of the control units is connected, the integrated apparatus including a signal processing unit that links images captured by the respective surgical imaging apparatuses.

REFERENCE SIGNS LIST

100 Camera unit
200 CCU
210 Signal processing unit
600 Integrated apparatus
1000 Surgical system

The invention claimed is:

1. A medical system comprising:
a plurality of surgical imaging apparatuses each having a different angle of view, the plurality of the surgical imaging apparatuses being physically separate apparatuses respectively; and
processing circuitry, to which each of the surgical imaging apparatuses is coupled, configured to
determine whether the plurality of the surgical imaging apparatuses image a same subject or different subjects concurrently, and
link images captured by respective ones of the plurality of the surgical imaging apparatuses in response to determining that the plurality of the surgical imaging apparatuses image the same subject concurrently, and not link the images captured by the respective ones of the plurality of the surgical imaging apparatuses in response to determining that the plurality of the surgical imaging apparatuses image the different subjects concurrently, wherein the processing circuitry is further configured to, in response to determining that the plurality of the surgical imaging apparatuses image the same subject concurrently, perform a process of adapting a shake amount between the images captured by the respective ones of the plurality of the surgical imaging apparatuses, by tracking a first image of the images with a shake in accordance with a second image of the images without a shake or with a shake less than the shake of the first image, and correcting the shake in the first image by removing a shake component in the first image in accordance with the second image, and the first image is captured by a first surgical imaging apparatus of the plurality of the surgical imaging apparatuses having a first angle of view, and the second image is captured by a second surgical imaging apparatus of the plurality of the surgical imagine apparatuses having a second angle of view different from the first angle of view.

2. The medical system according to claim 1, wherein the plurality of the surgical imaging apparatuses include at least two different types of surgical imaging apparatuses of an endoscope, an extracorporeal scope, a microscope, or a surgical field camera.

3. The medical system according to claim 1, wherein the processing circuitry is configured to switch whether or not to perform the linking, according to occurrence of an adjustment trigger.

4. The medical system according to claim 1, wherein
the processing circuitry is configured to perform a process for the linking according to occurrence of an adjustment trigger, and
the adjustment trigger occurs by a user operation.

5. The medical system according to claim 1, wherein
the processing circuitry is configured to:
obtain information regarding a state of an operating surgeon who performs a surgery; and
perform a process for the linking based on the obtained information.

6. The medical system according to claim 1, wherein
the processing circuitry is configured to:
obtain identification information for identifying the plurality of the surgical imaging apparatuses; and
perform a process for the linking based on the obtained identification information.

7. The medical system according to claim 1, wherein the processing circuitry is configured to perform a process of adapting colors between the images captured by the respective ones of the plurality of the surgical imaging apparatuses.

8. The medical system according to claim 1, wherein the processing circuitry is configured to perform a process of adapting brightness between the images captured by the respective ones of the plurality of the surgical imaging apparatuses.

9. The medical system according to claim 1, wherein the processing circuitry is configured to perform a process of adapting contrast between the images captured by the respective ones of the plurality of the surgical imaging apparatuses.

10. The medical system according to claim 1, wherein the processing circuitry is configured to perform a process of adapting resolution between the images captured by the respective ones of the plurality of the surgical imaging apparatuses.

11. The medical system according to claim 1, wherein the processing circuitry is configured to perform a process of adapting noise between the images captured by the respective ones of the plurality of the surgical imaging apparatuses.

12. The medical system according to claim 1, wherein the processing circuitry is configured to perform a process of adapting a depth of field between the images captured by the respective ones of the plurality of the surgical imaging apparatuses.

13. The medical system according to claim 1, wherein the processing circuitry is configured to perform a process of adapting a depth between stereoscopic images captured by the respective ones of the plurality of the surgical imaging apparatuses.

14. The medical system according to claim 1, wherein the processing circuitry is configured to perform a process of adapting an angle of view between the images captured by the respective ones of the plurality of the surgical imaging apparatuses.

15. The medical system according to claim 1, wherein the processing circuitry is configured to link an image captured by one of the plurality of the surgical imaging apparatuses with an image captured by another one of the plurality of the surgical imaging apparatuses as a reference.

16. The medical system according to claim 1, wherein the processing circuitry is configured to link images captured by the plurality of the surgical imaging apparatuses with an arbitrary desired image as a reference.

17. A control unit comprising:
processing circuitry, to which each of a plurality of surgical imaging apparatuses is coupled, configured to
determine whether the plurality of the surgical imaging apparatuses image a same subject or different subjects concurrently,
link images captured by respective ones of the plurality of the surgical imaging apparatuses in response to determining that the plurality of the surgical imaging apparatuses image the same subject concurrently, and not link the images captured by the respective ones of the plurality of the surgical imaging apparatuses in response to determining that the plurality of the surgical imaging apparatuses image the different subjects concurrently, wherein
each of the plurality of the surgical imaging apparatuses has a different angle of view, the plurality of the surgical imaging apparatuses being physically separate apparatuses respectively,
the processing circuitry is further configured to, in response to determining that the plurality of the surgical imaging apparatuses image the same subject concurrently, perform a process of adapting a shake amount between the images captured by the respective ones of the plurality of the surgical imaging apparatuses, by tracking a first image of the images with a shake in accordance with a second image of the images without a shake or with a shake less than the shake of the first image, and correcting the shake in the first image by removing a shake component in the first image in accordance with the second image, and
the first image is captured by a first surgical imaging apparatus of the plurality of the surgical imaging apparatuses having a first angle of view, and the second image is captured by a second surgical imaging apparatus of the plurality of the surgical imaging apparatuses having a second angle of view different from the first angle of view.

18. A medical system comprising:
a plurality of surgical imaging apparatuses each having a different angle of view, the plurality of the surgical imaging apparatuses being physically separate apparatuses respectively;
a plurality of control units, each of the plurality of the surgical imaging apparatuses being coupled to one of the plurality of the control units; and
an integrated apparatus to which each of the plurality of the control units is coupled, the integrated apparatus including processing circuitry configured to
determine whether the plurality of the surgical imaging apparatuses image a same subject or different subjects concurrently, and
link images captured by respective ones of the plurality of the surgical imaging apparatuses in response to determining that the plurality of the surgical imaging apparatuses image the same subject concurrently, and not link the images captured by the respective ones of the plurality of the surgical imaging apparatuses in response to determining that the plurality of the surgical imaging apparatuses image the different subjects concurrently, wherein
the processing circuitry is further configured to, in response to determining that the plurality of the surgical imaging apparatuses image the same subject concurrently, perform a process of adapting a shake amount between the images captured by the respective ones of the plurality of the surgical imaging apparatuses, by tracking a first image of the images with a shake in accordance with a second image of the images without a shake or with a shake less than the shake of the first image, and correcting the shake in the first image by removing a shake component in the first image in accordance with the second image, and
the first image is captured by a first surgical imaging, apparatus of the plurality of the surgical imaging, apparatuses having a first angle of view, and the second image is captured by a second surgical imaging apparatus of the plurality of the surgical imaging apparatuses having a second angle of view different from the first angle of view.

19. The medical system according to claim 1, wherein the first image is an endoscopic image captured by an endoscope, and
the second image is an stationary exoscopic image captured by an exoscope.

* * * * *